(12) United States Patent
Kurokawa et al.

(10) Patent No.: US 8,828,156 B2
(45) Date of Patent: Sep. 9, 2014

(54) ALUMINUM SHEET MATERIAL FOR LITHOGRAPHIC PRINTING PLATES

(75) Inventors: Shinya Kurokawa, Shizuoka (JP); Hirokazu Sawada, Shizuoka (JP); Akio Uesugi, Shizuoka (JP); Masanori Tsunekawa, Tokyo (JP); Kazuaki Hatano, Tokyo (JP); Hiroshi Ougi, Tokyo (JP); Koushi Nagae, Tokyo (JP)

(73) Assignees: Fujifilm Corporation, Minato-ku, Tokyo (JP); Sumitomo Light Metal Industries, Ltd., Minato-ku, Tokyo (JP)

( * ) Notice: Subject to any disclaimer, the term of this patent is extended or adjusted under 35 U.S.C. 154(b) by 542 days.

(21) Appl. No.: 12/802,742

(22) Filed: Jun. 11, 2010

(65) Prior Publication Data

US 2011/0039092 A1 Feb. 17, 2011

(30) Foreign Application Priority Data

Aug. 13, 2009 (JP) ................................. 2009-187667

(51) Int. Cl.
*C22C 21/00* (2006.01)
(52) U.S. Cl.
USPC ........................................... 148/437; 420/528
(58) Field of Classification Search
USPC ............................. 148/437; 420/528; 428/328
See application file for complete search history.

(56) References Cited

U.S. PATENT DOCUMENTS 4,003,738 A * 1/1977 Valdo .............................. 75/675
2009/0220376 A1 * 9/2009 Kernig et al. .................. 420/535

FOREIGN PATENT DOCUMENTS

WO WO 2007093605 A1 * 8/2007 ............. C22B 21/06

* cited by examiner

*Primary Examiner* — Brian Walck
(74) *Attorney, Agent, or Firm* — Flynn, Thiel, Boutell & Tanis, P.C.

(57) ABSTRACT

An aluminum sheet material for lithographic printing plates wherein the number of aluminum carbide particles having a circle equivalent diameter, measured by the PoDFA method, of 3 μm or more is four or less, the number of aluminum carbide particles having a circle equivalent diameter, measured by the PoDFA method, of 3 μm or more.

2 Claims, No Drawings

ALUMINUM SHEET MATERIAL FOR LITHOGRAPHIC PRINTING PLATES

BACKGROUND OF THE INVENTION

The present invention relates to an aluminum sheet material for lithographic printing plates that prevents swelling of a protective layer, particularly due to aluminum carbide, when used to produce a lithographic printing original plate.

A lithographic printing original plate produced by forming a lipophilic photosensitive resin layer on a hydrophilic support formed of an aluminum sheet material has been widely used. A desired printing plate has been normally obtained by performing mask exposure via a lith film, and dissolving and removing the non-image area.

In recent years, digitization technology that electronically processes, stores, and outputs image information using a computer has been widely used. A variety of new image output methods that deal with such digitization technology have been put to practical use. As a result, computer-to-plate (CTP) technology that directly produces a printing plate by scanning light with high directivity (e.g., laser light) based on digitized image information without using a lith film, has been used.

When producing a lithographic printing original plate using the CTP technology, a printing plate aluminum sheet material is subjected to a surface-roughening process (e.g., graining) and a sulfuric acid anodizing process, and a photosensitive resin layer and a protective layer are formed on the surface of the aluminum sheet material, followed by heating and exposure. However, the protective layer of the lithographic printing original plate may swell and cause an image defect (e.g., image loss) due to exposure failure. It was confirmed that an image defect (e.g., image loss) due to exposure failure occurs when swelling with a diameter of 50 μm or more occurs.

WO2007/093605 A1 discloses an aluminum sheet material for lithographic printing plates in which the aluminum carbide content is limited to less than 10 ppm on the assumption that the protective layer swells when aluminum carbide contained in the aluminum sheet material reacts with steam inside the protective layer to produce methane gas.

SUMMARY OF THE INVENTION

The inventors of the present invention focused on the above aluminum sheet material for lithographic printing plates for which the aluminum carbide content is specified, and double-checked the relationship between swelling of the protective layer and aluminum carbide contained in the aluminum sheet material. As a result, the inventors found that aluminum carbide present in the surface area of the aluminum sheet material provided with the photosensitive layer and the protective layer reacts with water to produce aluminum hydroxide (i.e., increase in volume), and moves the protective layer upward between the aluminum plate and the protective layer.

When producing a lithographic printing original plate using the CTP technology, the aluminum sheet material is washed with water when subjected to a surface-roughening process (e.g., graining) and a sulfuric acid anodizing process. Since the photosensitive resin layer and the protective layer formed on the surface of the aluminum sheet material have water permeability, water is present inside the protective layer. The inventors found that this also causes the reaction between aluminum carbide and water. Even if the aluminum carbide content is limited to less than 10 ppm, swelling with a diameter of 50 μm or more occurs when forming the protective layer or the like, so that a minute image loss with a dimension of about 50 μm occurs.

The inventors conducted tests and studies in order to find a method that prevents exposure failure due to swelling. As a result, the inventors found that it is most effective and important to reduce the size of aluminum carbide present in the aluminum sheet material.

The present invention was conceived based on the above findings. An object of the present invention is to provide an aluminum sheet material for lithographic printing plates that prevents swelling due to aluminum carbide mixed in the aluminum material when used to produce a lithographic printing original plate.

According to one aspect of the present invention, the above object is achieved by an aluminum sheet material for lithographic printing plates wherein the number of aluminum carbide particles having a circle equivalent diameter, measured by the PoDFA method, of 3 μm or more is four or less, the number of aluminum carbide particles having a circle equivalent diameter, measured by the PoDFA method, or 3 μm or more being measured by melting 3000 g of the aluminum sheet material in a crucible disposed in an electric furnace, filtering 2000 g of the molten metal through a dedicated filter, allowing 1000 g of the molten metal remaining on the filter to solidify, and measuring the number of aluminum carbide particles contained in inclusions in the molten metal deposited on the upper surface of the filter by observing a vertical section (14 mm×10 mm) of the solidified metal including the diameter (14 mm) of the filter in the center area of the filter up to a height of 10 mm above the filter using a microscope.

The present invention thus provides an aluminum sheet material for lithographic printing plates that prevents swelling due to aluminum carbide mixed in the aluminum material when used to produce a lithographic printing original plate.

DESCRIPTION OF EXEMPLARY EMBODIMENTS

Aluminum carbide is mixed into aluminum during a pyrometallurgical process, a melting process, a refining process, or a casting process. When forming a photosensitive layer and a protective layer on a rolled aluminum sheet material for lithographic printing plates to produce a lithographic printing original plate, aluminum carbide present in the surface layer of the aluminum sheet material reacts with water to produce aluminum hydroxide (increase in volume), and moves the protective layer upward so that an image defect (e.g., image loss) due to exposure failure occurs.

An aluminum sheet material for lithographic printing plates according to one embodiment of the present invention is characterized in that the number of aluminum carbide particles having a circle equivalent diameter, measured by the PoDFA method, of 3 μm or more is four or less.

The PoDFA (porous disc filtration apparatus) method is described in D. Doutre, B. Gariepy, J. P. Martin, G. Dube, "Aluminum Cleanliness Monitoring: Method and Applications in Process Development and Quality Control", pp. 1179-1195, Light Metals, 1985, and is well-known in the art as a method that measures inclusions in a metal.

In the present invention, the number of aluminum carbide particles having a circle equivalent diameter, measured by the PoDFA method, of 3 μm or more is measured by melting 3000 g of the aluminum sheet material in a crucible disposed in an electric furnace, filtering 2000 g of the molten metal through a dedicated filter, allowing 1000 g of the molten metal remaining on the filter to solidify, and measuring the number of aluminum carbide particles contained in inclusions in the molten metal deposited on the upper surface of the filter using a microscope.

More specifically, 3000 g of the aluminum sheet material is melted in an alumina crucible disposed in an electric furnace. A dedicated crucible that is provided with a dedicated filter (diameter: 25 mm) at the bottom is preheated to 800° C. in an electric furnace, and disposed in a PoDFA apparatus (hereinafter referred to as "chamber"). The molten metal is slowly poured into the dedicated crucible. A container that receives a molten metal that has passed through the filter, and a weighing apparatus that weighs the molten metal are provided under the chamber.

The inside of the chamber is pressurized (2 kg/cm$^2$) using air to filter the molten metal. When 2000 g of the molten metal has been filtered, pressurization is terminated. The chamber is then opened so that the molten metal is allowed to solidify. After the molten metal has solidified, the solidified metal is sampled together with the filter (thickness: 5 mm) up to a height of 10 mm above the filter. The sampled solidified metal has a diameter of 14 mm (i.e., the center area of the filter) and a height of 10 mm.

The vertical section (14 mm×10 mm) of the solidified metal including the above diameter of 14 mm is filled with a resin, and polished. The entire area (14 mm×10 mm) of the solidified metal is observed using an optical microscope (magnification: 500 to 1000) to determine the number of aluminum carbide ($Al_4C_3$) particles having a circle equivalent diameter of 3 μm or more. Aluminum carbide is identified in advance by elemental analysis (e.g., EPMA or EDS). Aluminum carbide is a black particle in the shape of a hexagonal column, and is observed as a hexagon or a rectangle in the observation plane.

The inventors conducted tests and studies on the number of aluminum carbide particles per unit weight contained in an aluminum sheet material that does not cause printing defects. As a result, the inventors found that printing defects can be industrially eliminated if the number of aluminum carbide particles observed in the observation plane is four or less.

If the circle equivalent diameter of aluminum carbide measured by the PoDFA method is less than 3 μm, swelling that causes exposure failure does not occur even if the aluminum carbide reacts with water to produce aluminum hydroxide (i.e., increase in volume).

Even if aluminum carbide having a circle equivalent diameter of more than 3 μm is mixed in the aluminum sheet material, the probability that aluminum carbide is present in the surface area of the aluminum sheet material and reacts with water so that an image defect (e.g., image loss) due to exposure failure occurs is almost zero in an industrial application, if the number of aluminum carbide particles having a circle equivalent diameter, measured by the PoDFA method, of 3 μm or more (hereinafter may be referred to as "aluminum carbide particles having a circle equivalent diameter of 3 μm or more") is four or less.

The aluminum sheet material according to one embodiment of the present invention is preferably produced by (1) utilizing an aluminum metal in which the number of aluminum carbide particles having a circle equivalent diameter of 3 μm or more is four or less as a raw material, (2) preventing a situation in which more than four aluminum carbide particles having a circle equivalent diameter of 3 μm or more are produced during the production process of the aluminum sheet material, or (3) removing aluminum carbide particles having a circle equivalent diameter of 3 μm or more during the production process, for example. A preferable production process is described below.

The aluminum sheet material for lithographic printing plates according to one embodiment of the present invention is produced by melting an aluminum alloy having a given composition, refining and casting the molten metal to obtain an ingot, and homogenizing, hot-rolling, and cold-rolling the ingot.

Aluminum carbide is contained in the aluminum metal as an impurity. Aluminum carbide is produced by the reaction between a carbon electrode used for electrolytic refining and the aluminum molten metal. It is preferable to utilize an aluminum metal in which the number of aluminum carbide particles having a circle equivalent diameter of 3 μm or more is four or less as the raw material. It was confirmed that most of the aluminum carbide mixed in the aluminum metal disappears by melting the aluminum metal in a melting furnace using fire.

It is more preferable to remove aluminum carbide particles having a circle equivalent diameter of 3 μm or more before casting by filtering the molten metal. In this case, it is preferable to use a rigid porous media filter that exhibits high filtration performance. Aluminum carbide particles having a circle equivalent diameter of 3 μm or more cannot be completely removed when using a rigid porous media filter (e.g., C-grade rigid porous media filter manufactured by NGK Insulators, Ltd., average pore size: 160 μm) that is normally used in an aluminum casting line. Therefore, a rigid porous media filter having a small mesh size (e.g., D-grade rigid porous media filter manufactured by NGK Insulators, Ltd., average pore size: 120 μm) is used to more effectively remove aluminum carbide. Most of the aluminum carbide particles having a circle equivalent diameter of 3 μm or more can be removed from the molten metal by passing 300 t or more of molten metal through the filter to form a cake layer having a sufficient thickness on the outer surface of the filter.

When filtering and casting a molten metal obtained by melting the raw material in a melting furnace, the aluminum molten metal comes in contact and reacts with carbon-containing parts (e.g., carbon-containing casting parts) to produce aluminum carbide during a refining step or a DC casting step. However, carbon-containing parts may necessarily be used in practical applications. Therefore, it is preferable to use parts (e.g., casting parts) that are formed of a dense carbon material and rarely react with the aluminum molten metal. When it is necessary to use parts that are formed of an inferior carbon material, it is preferable to apply a release agent to the surface of the carbon-containing parts or coat the carbon-containing parts with a heat-insulating protective material so that the carbon-containing parts do not come in contact with the aluminum molten metal.

Whether or not aluminum carbide particles having a circle equivalent diameter of 3 μm or more are present in the aluminum molten metal can be determined by the PoDFA method. The properties of the molten metal can be determined by evaluating the presence or absence and the size of aluminum carbide in the molten metal by the PoDFA method before the casting process, so that whether or not measures to prevent contact with the carbon-containing casting parts are necessary during the casting process can be determined.

An ingot obtained by the DC casting process is homogenized, hot-rolled, and cold-rolled to a given thickness. The resulting aluminum sheet material is subjected to an electrochemical etching process by the method described in paragraph 0024 of JP-A-2008-83383, subjected to a chemical etching process and a desmutting process by the method described in paragraph 0025 of JP-A-2008-83383, and subjected to an anodizing process by the method described in paragraphs 0026 and 0027 of JP-A-2008-83383. A photopolymerizable photosensitive layer and a protective layer described in paragraphs 0028 to 0168 of JP-A-2008-83383 are then formed to obtain a printing plate. An undercoat layer and an intermediate layer may optionally be formed before forming the photosensitive layer.

In order to determine the relationship between the size of aluminum carbide and swelling of the printing plate, an aluminum metal containing aluminum carbide particles having a circle equivalent diameter of 3 μm or more was melted, and cast using carbon-containing casting parts (without taking measures to prevent contact between the carbon-containing casting parts and the molten metal) to obtain an ingot. The ingot was homogenized, hot-rolled, and cold-rolled by a normal method to obtain an aluminum sheet material having a thickness of 0.24 mm.

The sheet material was subjected to a surface-roughening process by electrochemical etching using hydrochloric acid and nitric acid, a chemical etching process using sodium hydroxide, a desmutting process using sulfuric acid, and an anodizing process using sulfuric acid. These processes were performed by the methods described in paragraphs 0024, 0025, and 0026 of JP-A-2008-83383. The following intermediate layer coating liquid 1 was applied to the sheet material using a bar coater so that the amount after drying was 30 mg/m², and dried at 150° C. for 5 minutes.

Intermediate Layer Coating Liquid 1
Tetraethyl silicate: 4.0 parts by mass
Compound 1 (see below): 1.2 parts by mass
Compound 2 (see below): 11.0 parts by mass
Methanol: 5.0 parts by mass
Phosphoric acid aqueous solution (85%): 2.5 parts by mass Heat was generated after mixing and stirring the components for about 30 minutes. After stirring and reacting the components for 60 minutes, the following liquids were added to the mixture to prepare the intermediate layer coating liquid 1.
Methanol: 2000 parts by mass
1-Methoxy-2-propanol: 100 parts by mass

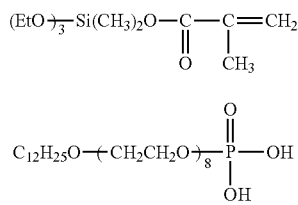

Compound 1

Compound 2

A photosensitive composition (1) having the following composition was applied to the intermediate layer using a bar coater, and dried at 90° C. for 1 minute to form a photosensitive layer. The mass of the photosensitive layer after drying was 1.35 g/m².

Photosensitive Composition 1
Addition polymerizable compound having an ethylenically unsaturated double bond ("PLEX 6661-O" manufactured by DEGUSSA): 1.69 parts by mass
Binder polymer (compound 3, mass average molecular weight: 80,000): 1.89 parts by mass
Sensitizing dye (40): 0.13 parts by mass
Hexaarylbiimidazole photoinitiator ("BIMD" manufactured by Kurogane Kasei Co., Ltd.): 0.46 parts by mass
ε-Phthalocyanine (F-1) (25 mass % methyl ethyl ketone dispersion): 1.70 parts by mass
Mercapto group-containing compound (SH-1): 0.34 parts by mass
Fluorine-containing nonionic surfactant ("Megafac F-780F" manufactured by DIC Corporation): 0.03 parts by mass
Cupferron. AL (polymerization inhibitor manufactured by Wako Pure Chemical Co., Ltd.) 10 mass % tricresyl phosphate solution: 0.12 parts by mass
Methyl ethyl ketone: 27.0 parts by mass
Propylene glycol methyl ether: 26.7 parts by mass

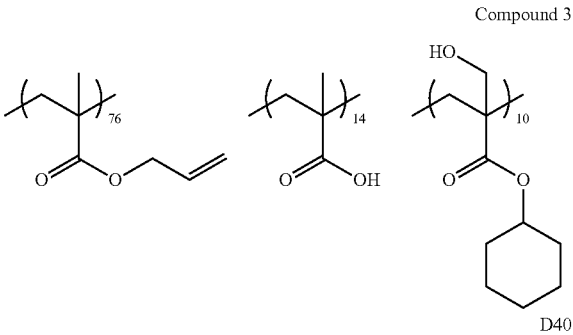

Compound 3

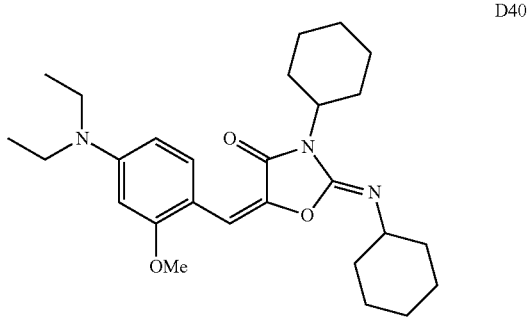

D40

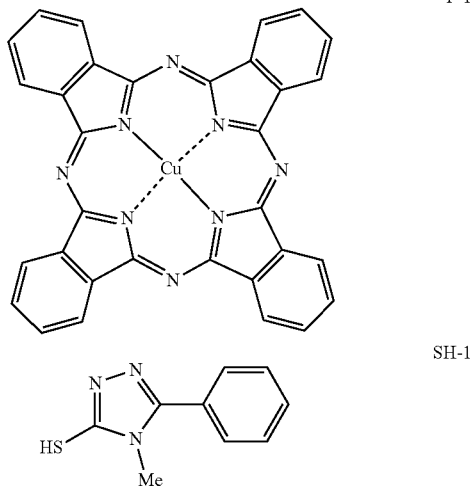

F-1

SH-1

A protective layer aqueous solution having the following composition was applied to the photosensitive layer using a bar coater so that the mass after drying was 2.5 g/m², and dried at 120° C. for 1 minute to obtain a lithographic printing original plate.

Protective Layer Aqueous Solution
Polyvinyl alcohol (degree of saponification: 95 mol %, degree of polymerization: 500)
Water-Soluble Resin (See Table 1)
Polymer (SP-1): 2.0 parts by mass
Luviskol VA64W (50% aqueous solution, manufactured by BASF): 1.2 parts by mass Nonionic surfactant ("Pionin D230" manufactured by Takemoto Oil & Fat Co., Ltd.): 2.0 parts by mass
Nonionic surfactant ("Emalex 710" manufactured by Nippon Nyukazai Co., Ltd.): 1.8 parts by mass
Water: 1100 parts by mass

SP-1

$$\left(\begin{array}{c}\\\end{array}\right)_{70}\quad \left(\begin{array}{c}\\\end{array}\right)_{15}\quad \left(\begin{array}{c}\\\end{array}\right)_{15}$$
COOCH$_3$  COOC$_2$H$_5$  CONHC(CH$_3$)$_2$CH$_2$SO$_3$Na

TABLE 1

| Water-soluble resin | Amount | Amount of polyvinyl alcohol (degree of saponification: 95 mol %, degree of polymerization: 500) |
|---|---|---|
| Luvitec VPC55K65W (manufactured by BASF) (Vinylpyrrolidone/vinylcaprolactam copolymer, aqueous solution (solid content: 30%)) | 46.5 parts by mass | 79.05 parts by mass |

The resulting lithographic printing original plate was allowed to stand for 30 days. The size of aluminum carbide was determined from the size of swelling formed on the surface of the lithographic printing original plate and a foreign object present in the swelling area. Table 2 shows the diameter of swelling and the maximum diameter (circle equivalent diameter) of aluminum carbide present in the swelling area.

TABLE 2

| Swelling area No. | Diameter of swelling area (μm) | Maximum diameter of aluminum carbide (μm) |
|---|---|---|
| 1 | 235 | 15 |
| 2 | 188 | 12 |
| 3 | 160 | 10 |
| 4 | 126 | 8 |
| 5 | 80 | 5 |
| 6 | 78 | 5 |
| 7 | 65 | 4 |
| 8 | 63 | 4 |
| 9 | 50 | 3 |
| 10 | 46 | 3 |
| 11 | 48 | 3 |
| 12 | 28 | 2 |
| 13 | 30 | 2 |
| 14 | 31 | 2 |

As shown in Table 2, aluminum carbide present in the swelling area having a large diameter had a large diameter. Aluminum carbide having a diameter of 4 μm or more was present in the swelling area having a diameter of more than 50 μm. Printing defects occur when a swelling area having a diameter of 50 μm or more occurs. The diameter of the swelling area was less than 50 μm when the maximum diameter of aluminum carbide present in the swelling area was less than 3 μm (swelling areas No. 12 to 14). In this case, an image defect (e.g., image loss) due to exposure failure does not occur. Aluminum carbide having a maximum diameter of 3 μm was present in the swelling area having a diameter of 50 μm (swelling area No. 9). However, the diameter of the swelling area could be reduced to less than 50 μm when the maximum diameter of aluminum carbide present in the swelling area was 3 μm (swelling areas No. 10 to 11).

EXAMPLES

Example 1

An aluminum metal shown in Table 1 was melted, refined under conditions shown in Table 4, and cast to obtain an ingot. The ingot was homogenized, hot-rolled, and cold-rolled by a normal method to obtain an aluminum sheet material having a thickness of 0.24 mm. In Table 4, the expression "prevention of contact with carbon-containing parts" refers to preventing contact with a stopper used during casting by providing a cover formed of heat-insulating fibers on the surface of a conical graphite stopper.

The resulting sheet material was used as a specimen. The maximum diameter (circle equivalent diameter) of aluminum carbide particles and the number of aluminum carbide particles having a circle equivalent diameter of 3 μm or more were measured by the PoDFA method. The aluminum carbide content was measured by gas chromatography analysis in accordance with the Light Metal Industrial Standard LIS-A07-1971. The specimen (420 mm×592 mm) was subjected to an etching surface-roughening process (see paragraphs 0031 to 0041 of JP-A-2008-83383) and an anodizing process. After forming an intermediate layer, a photosensitive layer, and a protective layer, the specimen was allowed to stand for 30 days. The maximum diameter of a swelling area formed on the surface of the specimen and the number of swelling areas having a diameter of 50 μm or more were measured. The results are shown in Table 5.

TABLE 3

| Metal No. | Maximum diameter of aluminum carbide (μm) | Aluminum carbide content (ppm) |
|---|---|---|
| A | 2 | 10 |
| B | 3 | 18 |
| C | 5 | 20 |
| D | 18 | 35 |

TABLE 4

| Method No. | Production method |
|---|---|
| a | Prevention of contact with carbon-containing parts + D-grade rigid porous media filter + formation of cake layer by passing 300 t of molten metal |
| b | Prevention of contact with carbon-containing parts + C-grade rigid porous media filter |
| c | C-grade rigid porous media filter |

TABLE 5

| Specimen No. | Metal | Production method | Maximum diameter of aluminum carbide in sheet material (μm) | Number of aluminum carbide particles having circle equivalent diameter of 3 μm or more | Aluminum carbide content in sheet material (ppm) | Maximum diameter of swelling area (μm) | Number of swelling areas having diameter of 50 μm or more (/0.25 m$^2$) |
|---|---|---|---|---|---|---|---|
| 1 | A | a | 2 | 0 | 6 | 29 | 0 |
| 2 | B | a | 2 | 0 | 11 | 30 | 0 |
| 3 | B | b | 3 | 4 | 12 | 48 | 0 |
| 4 | C | a | 3 | 8 | 9 | 55 | 15 |
| 5 | D | a | 15 | 19 | 11 | 238 | 70 |
| 6 | A | c | 5 | 23 | 13 | 80 | 86 |
| 7 | B | c | 4 | 31 | 16 | 64 | 123 |

As shown in Table 4, a swelling area having a diameter of 50 μm or more did not occur in specimens 1 to 3 according to the present invention. Specifically, the specimens 1 to 3 do not cause an image defect (e.g., image loss) due to exposure failure.

On the other hand, the diameter of a swelling area formed on the surface of specimens 4 and 5 was 50 μm or more, and the number of swelling areas increased. This is because the aluminum metal contained aluminum carbide having a large size, and the number of aluminum carbide particles having a circle equivalent diameter of 3 μm or more was large. The aluminum metal used for specimens 6 and 7 contained aluminum carbide having a small size. However, a large number of aluminum carbide particles having a circle equivalent diameter of 3 μm or more were produced due to contact with the carbon-containing parts during melting, refining, and casting. As a result, the diameter of a swelling area formed on the surface of specimens 6 and 7 was 50 μm or more, and the number of swelling areas increased.

What is claimed is:

1. An aluminum sheet material for lithographic printing plates wherein the number of aluminum carbide particles having a circle equivalent diameter measured by the PoDFA method of 3 μm or more is four or less, the number of aluminum carbide particles having a circle equivalent diameter measured by the PoDFA method of 3 μm or more being measured by melting 3000 g of the aluminum sheet material in a crucible disposed in an electric furnace, filtering 2000 g of the molten metal through a dedicated filter, allowing 1000 g of the molten metal remaining on the filter to solidify, and measuring the number of aluminum carbide particles contained in inclusions in the molten metal deposited on the upper surface of the filter by observing a vertical section (14 mm×10 mm) of the solidified metal including the diameter (14 mm) of the filter in the center area of the filter up to a height of 10 mm above the filter using a microscope.

2. A lithographic printing plate comprising the aluminum sheet material of claim 1 provided with a photosensitive layer and a protective layer thereon.

* * * * *